United States Patent
Del Soldato et al.

[11] Patent Number: 5,861,426
[45] Date of Patent: Jan. 19, 1999

[54] NITRO COMPOUNDS OF THE FORMULA A-$X_1$-$NO_2$ AND THEIR COMPOSITIONS HAVING ANTI-INFLAMMATORY, ANALGESIC AND ANTI-THROMBOTIC ACTIVITIES

[75] Inventors: Piero Del Soldato; Francesco Sannicolo, both of Milan, Italy

[73] Assignee: Nicox S.A., Paris, France

[21] Appl. No.: 737,426

[22] PCT Filed: Apr. 4, 1995

[86] PCT No.: PCT/EP95/01233

§ 371 Date: Mar. 6, 1997

§ 102(e) Date: Mar. 6, 1997

[87] PCT Pub. No.: WO95/30641

PCT Pub. Date: Nov. 16, 1995

[30] Foreign Application Priority Data

May 10, 1994 [IT] Italy .................................. MI94A0916
Aug. 9, 1994 [IT] Italy .................................. MI94A1731

[51] Int. Cl.⁶ ..................... C07D 487/04; C07D 333/22; A61K 31/40; A61K 31/405; C07C 203/04
[52] U.S. Cl. ..................... 514/413; 514/418; 514/509; 548/452; 549/76; 558/480; 558/482; 558/483; 534/660; 534/798

[58] Field of Search ...................... 558/482, 483, 558/480; 534/798, 660; 548/452; 546/76; 514/413, 418, 509

[56] References Cited

FOREIGN PATENT DOCUMENTS

| | | |
|---|---|---|
| 0549797 | 7/1993 | European Pat. Off. . |
| 92/01668 | 2/1992 | WIPO . |
| 94/04484 | 3/1994 | WIPO . |
| 94/12463 | 6/1994 | WIPO . |

*Primary Examiner*—Floyd D. Higel
*Attorney, Agent, or Firm*—Hale and Dorr LLP

[57] ABSTRACT

New compounds and their compositions having anti-inflammatory, analgesic and anti-thrombotic activities, of the general formula: A—$X_1$—$NO_2$ or their salts, wherein: A is $R(COX_u)_t$, wherein t is zero or 1 and u is zero or 1; and X is O, NH or $NR_{1C}$ wherein $R_{1C}$ is $C_1$–$C_{10}$ alkyl; and R is (Ia) wherein $R_1$ is acetoxoy, preferably n ortho-position with respect to —CO— and $R_2$ is hydrogen; or derivatives of acetylsalylsalicyclic acid; and $X_1$ is —YO— wherein Y is $C_1$–$C_{20}$ alkylene, $C_5$–$C_7$ cycloalkylene, oxy-alkyl derivatives and oxy-methyl benzyl derivatives.

40 Claims, No Drawings

NITRO COMPOUNDS OF THE FORMULA A-$X_f$-$NO_2$ AND THEIR COMPOSITIONS HAVING ANTI-INFLAMMATORY, ANALGESIC AND ANTI-THROMBOTIC ACTIVITIES

The present invention relates to new products having anti-inflammatory, analgesic and anti-thrombotic activities.

In particular it relates to inhibitors of cyclo-oxygenase (COX).

It is known that the anti-inflammatory and anti-thrombotic efficacy, but most of all the tolerance, of NSAIDs (Non Steroid Anti-Inflammatory Drugs), also known as FANS, seem to be considerably affected by their cyclo-oxygenase (COX)-inhibiting activity in the inflammatory site as well as in healthy tissue. See for example FASEB Journal 1, 89, 1987; Bioch. Biophys. Acta 1083, 1, 1991. It is generally believed that the more potent a COX inhibitor is the more effective it is.

The disadvantage of these products is that they are toxic.

Furthermore, it is also known that the COX-inhibiting properties seem to depend on some factors related to the physico-chemical and structural characteristics of the molecules themselves, such as for example the acidic function. See for example J. Pharmacol. Exp. Therap. 196, 226, 1976; Arch. Toxicol. 60, 261, 1987.

The known cyclo-oxygenase inhibitors are generally acids which can be brought back to general structures, including:

- carboxyl acids, either acetylated such as, for example, aspirin and triflusal, or nonacetylated such as, for example, salycilate, diflunisal, salsalate;
- acetic acids, for example diclofenac, indomethacin, tolmetin, sulindac, etodolac, ketorolac;
- propionic acids, such as, for instance, ibuprofen, naproxen, pirprofen, tiaprofenic acid, loxoprofen, indoprofen, oxaprozin, ketoprofen, fenoprofen, fenbufen, flurbiprofen, carprofen. suprofen;
- enolic acids, such as, for example, oxyphenbutazone, phenylbutazone, piroxicam, sudoxicam, tenoxicam, isoxicam, meloxicam.

See patents U.S. Pat. No. 3,558,690; U.S. Pat. No. 3,755,427; U.S. Pat. No. 3,641,127; FR 2,112,111; U.S. Pat. No. 4,035,376; U.S. Pat. No. 3,997,669; U.S. Pat. No. 3,784,701; U.S. Pat. No. 3,896,145; U.S. Pat. No. 3,600,437; U.S. Pat. No. 3,843,681; U.S. Pat. No. 3,904,682; U.S. Pat. No. 3,228,831; U.S. Pat. No. 4,161,538; U.S. Pat. No. 4,233,299; U.S. Pat. No. 3,591,584; DE 2,537,070; U.S. Pat. No. 3,161,654; U.S. Pat. No. 4,061,779; U.S. Pat. No. 4,556,672; U.S. Pat. No. 4,089,969.

The disadvantage of these products is that they are very effective but highly toxic.

The importance of the acidic function lies in the fact that a masking of this function in COX inhibitors results in a virtually complete loss of its prostanoid-inhibiting properties. See Drugs 35, 504, 1988.

Also known are products which are highly effective in inhibiting cyclooxygenase and have a low toxicity even though they do not contain the acidic function in their molecule.

These products are known as nitric esters with nonacidic ending. See for example patents PCT WO 94/04484, which describes a particular group of compounds including the well known commercial product diclofenac; PCT/EP 93/03193, which describes another specific group of compounds including the commercial products flurbiprofen and indoprofen.

The Applicant has unexpectedly found that other compounds having the termination group —$ONO_2$, when $X_1$=—$YO$—, as defined hereinafter, have anti-inflammatory, analgesic and anti-thrombotic activities when used as medicaments with high efficacy in cyclo-oxigenase inhibition and have low toxicity.

A further object of the invention is that the known products as reported in PCT WO 94/04484 and PCT/EP 93/03193 and the new compounds found by the Applicant having $X_1$=—$YO$— have a pharmaco-dynamic disadvantage. In fact, in the biochemical test evaluating the cyclo-oxygenase-inhibiting activity, experiments conducted by the applicant showed a high response variability, in the order of 10–40%.

This generally results in an erratic and unpredictable efficacy, so that the determination of a correct dosage is difficult.

In practice, higher doses must be administered to limit the above variability. The disadvantage lies in the risks of a higher incidence of side effects.

Another disadvantage is that these products are difficult from a formulation point of view because oral or parenteral preparations are more difficult to prepare than traditional preparations based on acidic FANS.

Molecule solubility is known be one of the most important properties affecting the molecule pharmacokinetic and dynamic processes.

For example, for parenteral administration, particularly by the intravenous route, drugs must be formulated in soluble form.

Similarly, by the oral route, the solubilisation process is decisive for absorption and interaction with the effector.

In this respect, the choice of particular solvents and/or excipients, including surfactants, etc., is also toxicologically critical. For example, an intravenous formulation should not cause haemolysis or incompatibility with blood constituents.

However, there is much evidence which indicates that surfactants and apolar solvents may be irritant. See, for instance, J. Pharm. Science 72, 1014, 1983.

Trials conducted by the applicant using 0.1% Tween 80 and 1% dimethylsulphoxide to suspend nitroxybutylflurbiprofen showed that this solvent was irritant to the gastric mucous membrane.

However, it was unpredictably found that, using a NO-flurbiprofen derivative as described below which is part of the object of the present invention, the amounts of Tween 80 and dimethylsulphoxide required for suspension were lower, such that no irritant effects were caused, even though results were the same in terms of solubilisation.

It was unpredictably and surprisingly found after numerous investigations that it is possible to prepare anti-inflammatory products, as described below, having a high cyclo-oxygenase-inhibiting activity combined with low toxicity and pharmacokinetically satisfactory responses, and having a very limited response variability with an average variation coefficient of about one half that of known products pharmacodynamically, and easier to formulate as oral or parenteral preparations.

This was totally surprising and unexpected as the factors which affect the anti-inflammatory and anti-thrombotic efficacy of NSAIDs depend on a number of parameters. Therefore, it is not possible to forecast pharmacokinetics, for example the product fraction absorbed, the pharmacodynamic activity, the toxicity and the COX-inhibiting properties and, most of all, no assumptions may be made to predict or limit response variability.

Object of the present invention are compounds, or their compositions, of general formula:

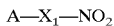

or their salts, for use as medicaments, in particular as anti-inflammatory or antithrombotic agents, wherein:

$A=R(COX_u)_t$, wherein t is zero or 1; u is zero or 1, X=O, NH, $NR_{1C}$ wherein $R_{1C}$ is a linear or branched alkyl having 1 to 10 C atoms;

R is chosen from the following groups:

group I), wherein t=1 and u=1

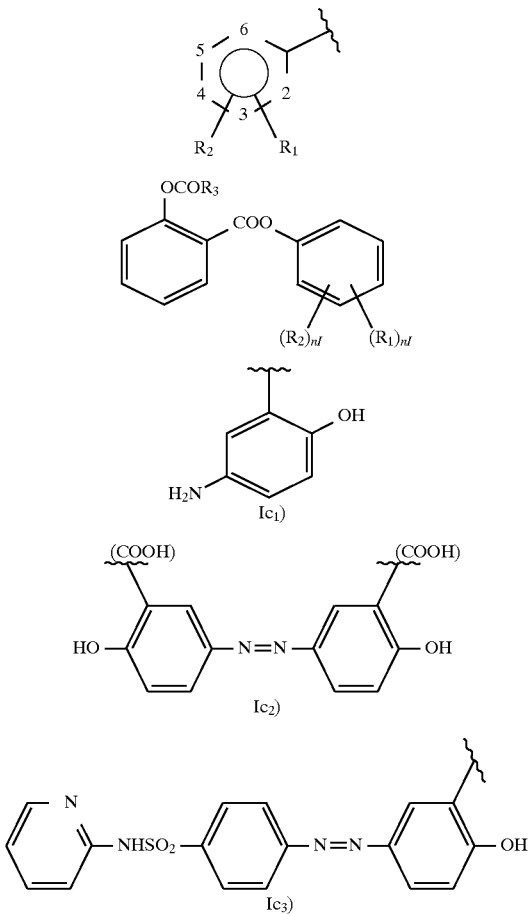

wherein:

- $R_1$ is an $OCOR_3$ group, wherein $R_3$ is methyl, ethyl or a linear or branched $C_3$–$C_5$ alkyl, or the residue of a heterocycle with a single ring having 5 or 6 atoms which may be aromatic, partially or totally hydrogenated, containing one or more heteroatoms independently chosen from O, N, and S;
- $R_2$ is hydrogen, hydroxy, halogen, a linear or when permissible branched alkyl having 1 to 4 C atoms, a linear or when permissible branched alkoxyl having 1 to 4 C atoms, a linear or when permissible branched perfluoroalkyl having 1 to 4 C atoms, for example trifluoromethyl, nitro, amino, mono- or di-$(C_{1-4})$ alkylamino;
- $R_1$ and $R_2$ together are a dioxymethylene group, with the provisos that when X=NH, then $X_1$ is ethylene and $R_2$=H; $R_1$ cannot be $OCOR_3$ in position 2 when $R_3$ is methyl; nI being 0 or 1.

Preferably, in Ia) X is equal to O or —NH, $R_1$ is acetoxy, preferably in ortho-position, with respect to —CO—, $X_1$ is $(CH_2—CH_2—O)_2$, $R_2$ is hydrogen, most preferred are the following $A—X_1—NO_2$ compounds: 3-acetoxy-N-(2-nitroxyethyl)-benzamide, 4-acetoxy-N-(2-nitroxyethyl)-benzamide, 3-acetoxy-N-(5-nitroxypentyl)-benzamide; 2-acetoxy-n-(5-nitroxypentyl)benzamide, N-2-(nitroxyethyl)-2-propionoxy-benzamide, 2-acetoxy-2-nitroxy-ethyl benzoate, 2-acetoxy-N-(cis-2-nitroxycyclohexyl)-benzamide, 2-acetoxy-4-chloro-N-(2-nitroxyethyl)-benzamide, N-(2-nitroxyethyl)-2-((4-thiazolyldinyl)carbonyloxy)-benzamide hydro chloride, 2-nicotinoyloxy-N-(2-nitroxyethyl)-benzamide, 2-acetoxy-5-nitroxypentylbenzoate;

preferably, in Ib) $R_3=CH_3$, nI=0;

X is equal to O, $X_1$ is ethylene: in this case Ib) is the residue of acetylsalicylsalicylic acid;

Compounds Ic) of the class $Ic_1$) 5-amino salicylic acid derivatives (5-amino-2-hydroxybenzoic acid) are known as mesalamine when the valence is saturated with —COOH. In compounds $Ic_2$) at least one of the —COOH is reacted to form the compounds of the invention. When both —COOH are reacted one obtains bifunctional compounds. When the compound is saturated with —COOH, is known as olsalazine.

Compounds $Ic_3$) are known, when the starting radical has a —COOH as sulfasalazine: 2-hydroxy-5-[(4-[(2-pyridinylamino)sulphonyl]phenyl]azo]benzoic acid.

The preferred compounds of Ic) have X=O and u=1 and $X_1$ is different from —YO—.

group II) wherein t=1, u=1

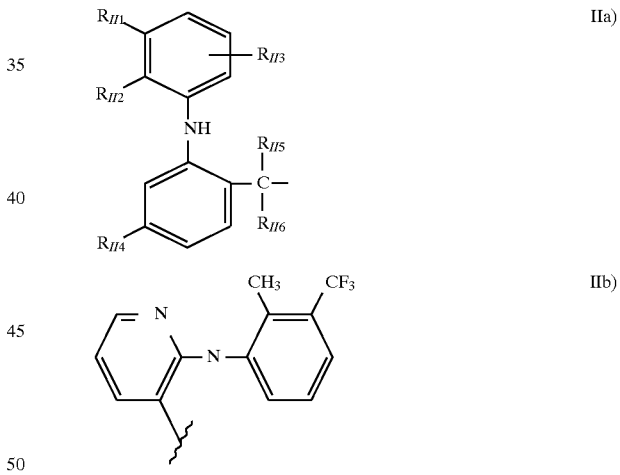

wherein:

- $R_{II5}$ is H, a linear or branched $C_1$–$C_3$ alkyl when permissible $R_{II6}$ has the same meaning as $R_{II5}$, or, when $R_{II5}$ is H, it may be benzyl;
- $R_{II1}$, $R_{II2}$ and $R_{II3}$ independently from one another are hydrogen, a linear or when permissible branched $C_1$–$C_6$ alkyl, or $C_1$–$C_6$ alkoxy, or Cl, F, Br;
- $R_{II4}$ is $R_{II1}$ or bromine;
- preferred are the compounds wherein $R_{II1}$, $R_{II2}$ and $R_{II4}$ are H and $R_{II3}$ is chlorine and $R_{II3}$ is in the ortho position relative to NH;
- $R_{II5}$ and $R_{II6}$ are H, X is equal to O, and $X_1$ is $(CH_2—CH_2—O)_2$;
- IIb) is the residue of 2-[(2-methyl-3-(trifluoromethyl) phenyl]amino]-3-pyridinecarboxylic acid] and when —COOH is present is known as flunixin.

Preferred compounds are those in which u=1 and X=O.

group III), wherein t=1, u=1 and R is:

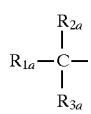

wherein:

$R_{2a}$ and $R_{3a}$ are H, a linear or when permissible branched, substituted or non-substituted $C_1$–$C_{12}$ alkyl, allyl, with the proviso that when one of the two groups is allyl, the other is H; preferably $R_{2a}$ is H, an alkyl having from 1 to 4 C, $R_{3a}$ is H;

$R_{1a}$ is chosen from

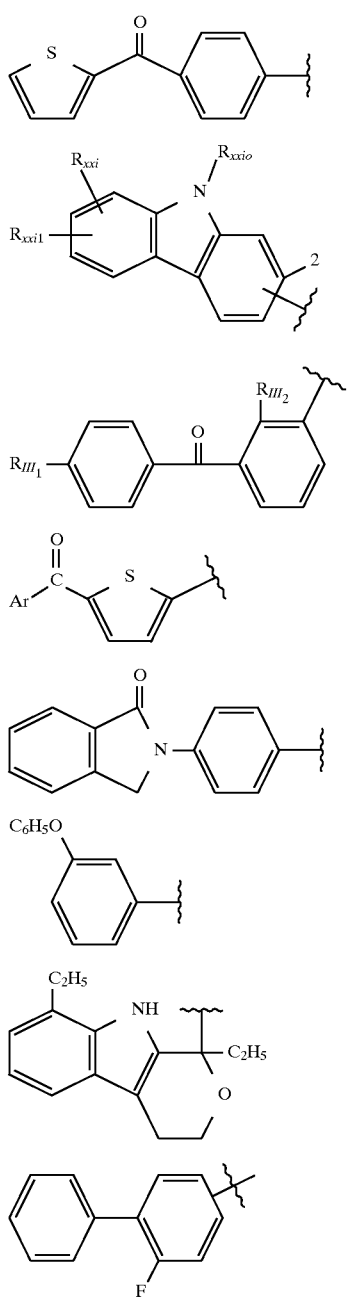

III D) has the following compounds:

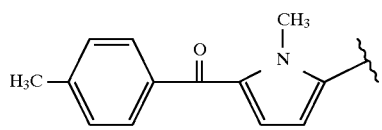

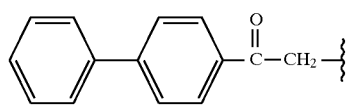

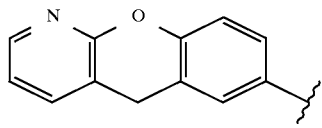

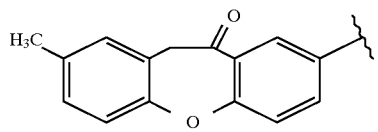

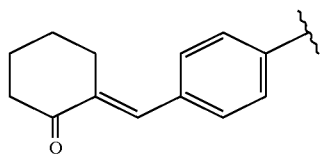

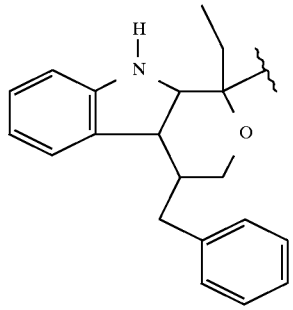

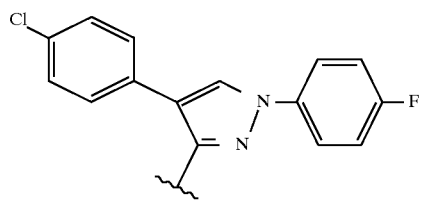

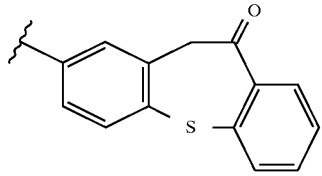

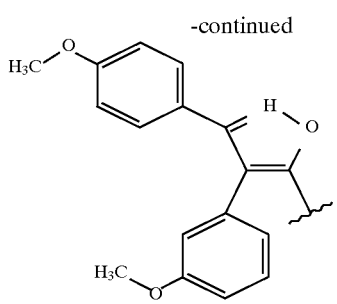

(XXXVII)

wherein the meanings are as follows:
in the compound of formula (IV), residue of Ketoprofen:
$R_{III1}$ is H, $SR_{III3}$ wherein $R_{III3}$ contains from 1 to 4 C atoms, linear or when permissible branched;
$R_{III2}$ is H, hydroxy;
preferred are the compounds wherein $R_{III1}$ and $R_{III2}$ are H, $R_{3a}$ is H and $R_{2a}$ is methyl, X=O;
in the compounds of formula (XXI) residue of carprofen:
$R_{XXio}$ is H, a linear or when permissible branched alkyl having from 1 to 6 C atoms, a $C_1$–$C_6$ alkoxycarbonyl bound to a $C_1$–$C_6$ alkyl, a $C_1$–$C_6$carboxylalkyl, a $C_1$–$C_6$ alkanoyl, optionally substituted with halogens, benzyl or halobenzyl, benzoyl or halobenzoyl;
$R_{XXi}$ is H, halogen, hydroxy, CN, a $C_1$–$C_6$ alkyl optionally containing OH groups, a $C_1$–$C_6$ alkoxy, acetyl, benzyloxy, $SR_{XXi2}$ wherein $R_{XXi2}$ is an alkyl $C_1$–$C_6$; a perfluoroalkyl having from 1 to 3 C atoms, a $C_1$–$C_6$ carboxyalkyl optionally containing OH groups, $NO_2$, ammino, sulphamoyl, a dialkyl sulphamoyl with the alkyl having from 1 to 6 C atoms, or a difluoroalkylsulphonyl with the alkyl having from 1 to 3 C atoms;
$R_{XXi1}$ is halogen, CN, a $C_1$–$C_6$ alkyl containing one or more OH groups, a $C_1$–$C_6$ alkoxy, acetyl, acetamide, benzyloxy, $SR_{III3}$ as above defined, a perfluoroalkyl having from 1 to 3 C, hydroxy, a carboxyalkyl having from 1 to 6 C, $NO_2$, ammino, a mono- or di-alkylamino having from 1 to 6 C, sulphamoyl, a di-alkyl sulphamoyl having from 1 to 6 C, or a difluoroalkylsulphamoyl as above defined; or $R_{XXi}$ together with $R_{XXi1}$ is an alkylene dioxy having from 1 to 6 C;
preferred are the compounds wherein $R_{XXio}$ is H, the connecting bridge is in position 2, $R_{XXi}$ is H, $R_{XXi1}$ is chlorine and is in the para position relative to nitrogen;
$R_{3a}$ is H, $R_{2a}$ is methyl and X is O;
in the compounds of formula (XXXV), residue of tiaprofenic acid:
Ar is phenyl, a hydroxyphenyl optionally mono- or poly-substituted with halogen, an alkanoyl and an alkoxy having from 1 to 6 C, a trialalkyl having from 1 to 6 C, preferably from 1 to 3 C, cyclo-pentyl, cylo-hexyl, cyclo-heptyl, heteroaryl, preferably thienyl, a furyl optionally containing OH, pyridyl;
the preferred (XXXV) compounds are those wherein Ar is phenyl, $R_{3a}$ is H, $R_{2a}$ is methyl and X is O;
in the compound of formula (II), residue of suprofen, of which the one preferred has been shown, wherein $R_{3a}$ is H, $R_{2a}$ is methyl and X=O; its equivalents as described and obtained in U.S. Pat. No. 4,035,376, which is incorporated herein in full as a reference, may also be used;
in the compound of formula (VI),
of which the ones preferred indoprofen, when $R_{2a}$ is $CH_3$ and indobufen when $R_{2a}$ is equal to H, $R_{3a}$=—$CH_3$ and X=O have been shown;

its equivalents as described in and obtained in accordance with U.S. Pat. No. 3,997,669, which is incorporated herein in full as reference, may also be used;
in the compounds of formula (VIII),
of which the one preferred, etodolac, wherein $R_{2a}$=$R_{3a}$=H and X=O has been shown; its equivalents as described in and obtained in accordance with U.S. Pat. No. 3,843,681, which is incorporated herein in full as reference, may also be used;
in the compounds of formula (VII),
of which the one preferred, fenoprofen, wherein $R_{3a}$=X, $R_{2a}$=—$CH_3$ and X=O has been shown; its equivalents as described in and obtained in accordance with U.S. Pat. No. 3,600,437, which is incorporated herein in full as reference, may also be used;
in the compounds of formula (III),
of which the preferred, fenbufen, wherein $R_{2a}$=$R_{3a}$=H and X=O has been shown; its equivalents as described in and obtained in accordance with patent U.S. Pat. No. 3,784,701, which is incorporated herein in full as a reference, may also be used;
in the compounds of formula (IX), residue of flurbiprofen wherein $R_{3a}$ is H, $R_{2a}$ is —$CH_3$ and X=O;
in the compounds of formula (X), residue of tolmetin, wherein $R_{2a}$=$R_{3a}$=H and X=O;
its equivalents as described in and obtained in accordance with patent FR 1,574,570, which is incorporated herein in full as a reference, may also be used;
In class III D) the meaning is the following:
IIIa) when it contains the —CH($CH_3$)—COOH is known as pranoprofen: α-methyl-5H-[1]benzopyrano [2,3-b] pyridine-7-acetic acid.
In the preferred compound $R_{2a}$=H, $R_{3a}$=$CH_3$, u=1 and X=O.
The residue (XXX) when contains —CH($CH_3$)—COOH is known as bermoprofen: dibenz[b, f]oxepin-2-acetic acid.
The preferred compound has u=1, X=O, $R_{2a}$=H, $R_{3a}$=$CH_3$.
The residue of (XXXI) is known as CS-670: 2-[4-(2-oxo-1-cyclohexylidenemethyl)phenyl]propionic acid, when the radical is —CH($CH_3$)—COOH.
The preferred compound has $R_{2a}$=H, $R_{3a}$=$CH_3$, u=1, X=O.
The residue (XXXII) derives from the known pemedolac which contains the —$CH_2$COOH groups.
The preferred compound has $R_{2a}$=$R_{3a}$=H, u=1, X=O.
This residue (XXXIII) is known as pirazolac when is saturated with —$CH_2$COOH:
4-(4-chlorphenyl)-1-(4-fluorphenyl)3-pyrazolyl acid derivatives.
Preferred compounds have $R_{2a}$=$R_{3a}$=H, u=1 and X=O.
The residue (XXXVI) when saturated with —CH($CH_3$)—COO—, is known as zaltoprofen.
When the residue is saturated with an hydroxy or an amino group or the salts of the acid, the compounds are known as dibenzothiepin derivatives.
The preferred products have a $R_{2a}$=H, $R_{3a}$=$CH_3$, u=1, X=O.
The residue (XXXVII) is deriving from the known mofezolac: 3,4-di(p-methoxyphenyl)isoxazol-5-acetic acid when the residue is —$CH_2$—COOH.

Preferred compounds $R_{2a}=R_{3a}=H$, $t=1$, $X=O$.

group IV) in which $t=1$, $u=1$ and R is

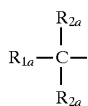

wherein:
$R_{IVd}$ and $R_{IVd1}$ are at least one H and the other a linear or when permissible branched $C_1$–$C_6$ alkyl, preferably $C_1$ and $C_2$, or a difluoroalkyl with the alkyl having from 1 to 6 C, $C_1$ is preferred, or $R_{IVd}$ and $R_{IVd1}$ together form a methylene group;

$R_{IV}$ has the following meaning:

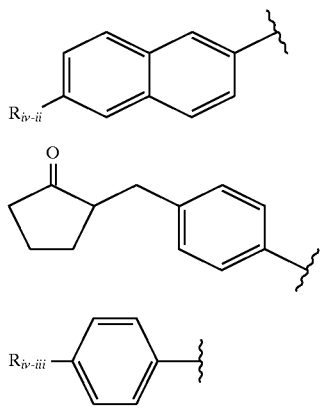

wherein the compounds of group IV) have the following meanings:
in the compounds of formula (II):
$R_{iv\text{-}ii}$ a 1–6 C alkyl, a cycloalkyl having from 3 to 7 C, an alkoxymethyl having from 1 to 7 C, a trifluoroalkyl having from 1 to 3 C, vinyl, ethinyl, halogen, an alkoxy having from 1 to 6 C, a difluoroalkoxy with the alkyl having from 1 to 7 C, an alkoxymethyloxy having from 1 to 7 C, an alkylthiomethyloxy with the alkyl having from 1 to 7 C, an alkyl methylthio with the alkyl having from 1 to 7 C, cyano, difluoromethylthio, phenyl- or phenylalkyl substituted with the alkyl having from 1 to 8 C;
preferably $R_{iv\text{-}ii}$ is —$CH_3O$, $R_{IVd}$ is H and $R_{IVd1}$ is —$CH_3$, and is known as a residue of naproxen;
X=NH and $X_1$ is equal to —$(CH_2$—$CH_2$—$O)_2$; also preferred is the same compound wherein X is equal to O;
in the compounds of formula (X),
of which the residue of loxoprofen has been shown, the residues described in U.S. Pat. No. 4,161,538, which is incorporated herein in full as a reference, may be used as equivalents. Preferred are the compounds in which $R_{IVd}$ is H and $R_{IVD1}$ is $CH_3$, X=NH and $X_1$ is equal to $(CH_2$—$CH_2$—$O)_2$; also preferred is the same compound wherein X is equal to O;
in the compounds of formula (III):
$R_{iv\text{-}iii}$ is a $C_2$–$C_5$ alkyl, even branched whenever possible, a $C_2$ and $C_3$ alkyloxy, allyloxy, phenoxy, phenylthio, a cycloalkyl having from 5 to 7 C atoms, optionally substitutes in position 1 by a $C_1$–$C_2$ alkyl;

preferred is the compound wherein $R_{iv\text{-}iii}$ is

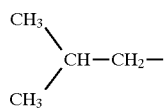

and $R_{IVd}$=H, $R_{IVd1}$ is —$CH_3$, a compound known as a residue of ibuprofen;
X=NH and $X_1$ is equal to $(CH_2$—$CH_2$—$O)_2$; also preferred is the same compound wherein X is equal to O;

group V)

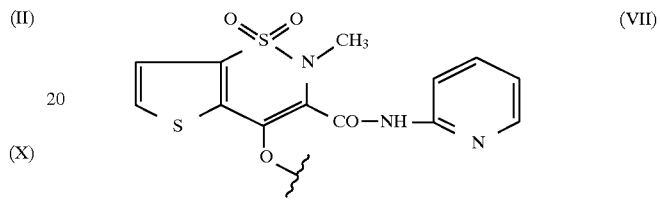

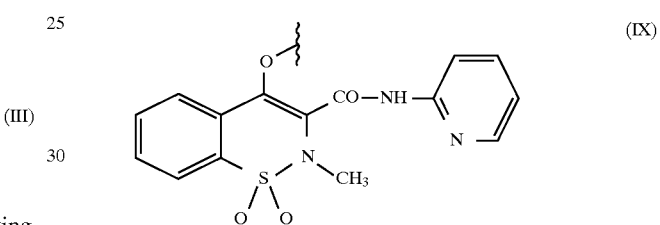

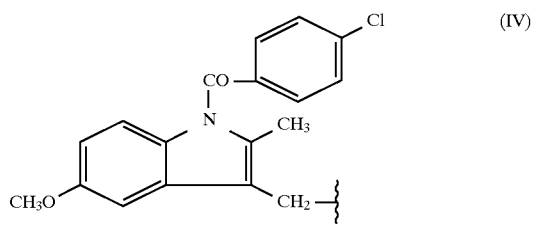

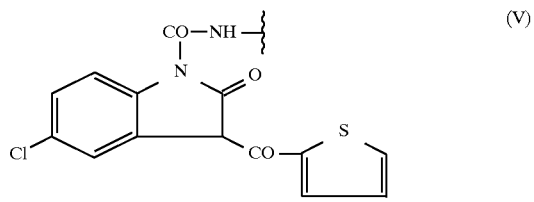

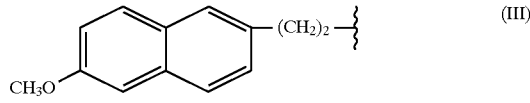

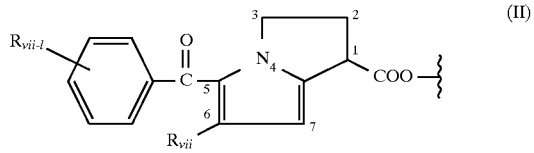

Class VE)

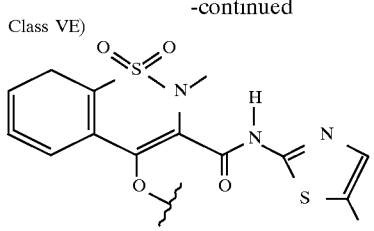
(X)

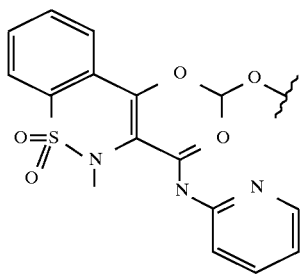
(XI)

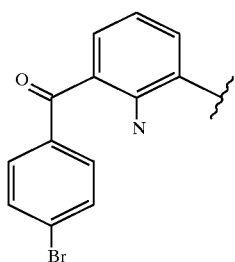
(XII)

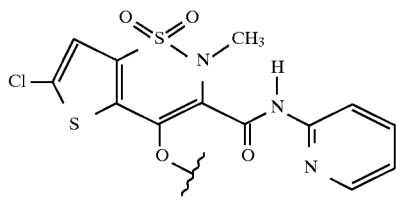
(XIII)

In group V), the compounds have the following meanings:
in the compounds of formula (II)
$R_{vii}$ is H or a linear or when permissible branched alkyl having from 1 to 4 C;
$R_{vii-1}$ is $R_{vii}$ or a linear or when permissible branched alkoxy having from 1 to 4 C; Cl, F, Br; the position of $R_{vii-1}$ being o-,m- or p-;
preferred is the residue of the known ketorolac, wherein $R_{vii}$ and $R_{vii-1}$ are H, and A=R and t=0
in the compounds of formula (V),
of which the residue of the known tenidap has been shown, its equivalents as described and obtained in U.S. Pat. No. 4,556,672, which is incorporated herein in full as a reference, may also be used;
in these compounds of formula (V) A=R and t=0,
in the compounds of formula (VII)
of which the residue of the known tenoxicam has been shown, A is RCO and t=1 and u=0 or A is R and t=0; its equivalents as described and obtained in patent DE 2,537,070, which is incorporated herein in full as a reference, may also be used;
in the compounds of formula (IX)
where A=R and t=0, or A=RCO with t=1 and u=0, of which the residue of the known piroxicam has been shown, its equivalents as described and obtained in U.S. Pat. No. 3,591,584, which is incorporated herein in full as a reference, may also be used;

in the compounds of formula (III)
where A=RCOO, t=1 and u=0 or 1; or t=0 and A=R, of which the residue of the known nabumetone has been shown, its equivalents as described and obtained in U.S. Pat. No. 4,061,779, which is incorporated herein in full as reference, may also be used;
in the compounds of formula (IV)
where A=RCOO, t=1, u=1 of which the residue of the known indomethacin has been shown, its equivalents as described and obtained in U.S. Pat. No. 3,161,654, which is incorporated herein in full as reference, may also be used.
in compounds of formula (X):
the residue (X) is known as meloxicam.
Preferred compounds are those in which t=0.
The residue (XI) is known as ampiroxicam when the termination is —$COOC_2H_5$.
The preferred compounds have u=1 and X=O; or t=0.
The residue (XII) when is saturated with —$CH_2COO$— is known as bromfenac.
The preferred compounds have u=1, X=O and $R_{2a}=R_3a=H$; or t=0.
The residue XIII) derives from the known Lornoxicam when the valence is saturated with H.
Preferred compounds have t=0.
$X_1$ in the formula A—$X_1$—$NO_2$ is a bivalent connecting bridge chosen from the following:
—YO—
where Y is:
a linear or when permissible branched $C_1$–$C_{20}$ alkylene, preferably having from 2 to 5 carbon atoms, excluding this connecting bridge when R is:
a radical of group I) except class Ib) and Ic);
a radical of group II) except $II_b$);
a radical of group III) except class of compounds of IIID)
a radical of group IV);
a radical of group V), except X) and including —($CH_2$)$_4$— for the compounds of formulae (III) and (IV);
or a cycloalkylene having from 5 to 7 carbon atoms optionally substituted;

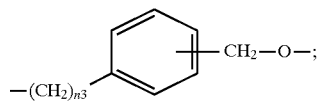

wherein $n_3$ is 0 or an integer from 1 to 3

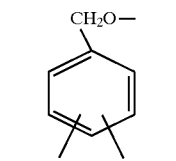

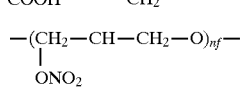

wherein nf is an integer from 1 to 6, preferably from 1 to 3;

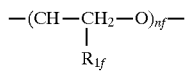

wherein $R_{1f}$=H, —$CH_3$ and nf is an integer from 1 to 6, preferably from 2 to 4.

The compounds containing R of group I of type Ia) are described in patent WO92/01668 wherein the preparation methods are also described. This patent is incorporated herein in full as a reference. The compounds of type Ib) are prepared, for instance, using the method described in the Merck Index, XI Ed., 1989, page 16, n.95, for the residue of acetylsalicylsalicylic acid. The changes in the compounds of formula Ib) may be obtained applying the processes described in patent WO 92/01668.

Compounds Ic) of the class $Ic_1$), in which the radical is a 5-amino salicylic acid derivative (5-amino-2-hydroxybenzoic acid) known as mesalamine, when the starting radical contains —COOH, are prepared by reduction of m-nitrobenzoic acid with Zn dust and HCl (see H. Weil et al., Ber. 55B, 2664 (1922)); or by electrolitic reduction: Le Guyader, Peltier, Compt. Rend. 253, 2544 (1961). These publications are incorporated here by reference.

The starting radical $Ic_2$) when it contains —COOH is known as olsalazine: 3,3'-azobis(6-hydroxybenzoic acid); and it is prepared according to EP 36,636 or U.S. Pat. No. 4,528,367, here both incorporated by reference.

Compounds $Ic_3$) are prepared according to U.S. Pat. No. 2,396,145 here incorporated by reference.

Equivalent compounds to $Ic_1$), $Ic_2$) and $Ic_3$) contain the substituents indicated in the above references.

The products of the present invention having the general formula

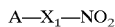

with the connecting bridges $X_1$ as above defined, with respect to the compounds of group I), may be obtained using the above methods of the known art or changing the known methods by introducing bridges $X_1$ when these are different from the connecting bridges described in the above patents.

The compounds wherein R is of group II) are described in patents WO94/04484 and U.S. Pat. No. 3,558,690 wherein the preparation methods are also described. These patents are incorporated herein in full as a reference.

The starting compound of IIb), when the valence is saturated with —COOH (flunixin), is obtained according to U.S. Pat. No. 3,337,570 and U.S. Pat. No. 3,689,653 here incorporated by reference. Compounds containing the substituents indicated in the above patents are equivalent to flunixin.

With respect to the compounds of group II), the connective bridges $X_1$ as above defined may be obtained using the above methods of the known art or changing the known methods by introducing bridges $X_1$ when these are different from the connecting bridges described in the above patents.

The compounds wherein R is of group III) are described and obtained by the processes explained in the following patents: patent application PCT/EP/93 03193; for the compounds of formula (IV) also see U.S. Pat. No. 3,641,127; for the compounds of formula (XXI) also see U.S. Pat. No. 3,896,145; for the compounds of formula (IX), residue of flurbiprofen, also see U.S. Pat. No. 3,755,427; for the compounds of formula (II) also see U.S. Pat. No. 4,035,376; for the compounds of formula (VI) also see U.S. Pat. No. 3,997,669; for the compounds of formula (VIII) also see U.S. Pat. No. 3,843,681; for the compounds of formula (VII) also see U.S. Pat. No. 3,600,437; for the compounds of formula (III) also see U.S. Pat. No. 3,784,701. All these patents are incorporated herein in full as a reference.

The processes for the preparation of compounds of class III D) are the following:

IIIa) residue is obtained by preparing the acid compound, according to U.S. Pat. No. 3,931,205, the valence is saturated with —$CH(CH_3)$—COOH. Compounds containing the substituents indicated in the above patent are equivalent to pranoprofen.

The residue (XXX) is prepared through the compound with —$CH(CH_3)$—COOH (bermoprofen) according to U.S. Pat. No. 4,238,620 here incorporated by reference. Other equivalent products are listed in the above patent.

The residue (XXXI) is prepared by starting from the corresponding acid —$CH(CH_3)$—COOH, according to U.S. Pat. No. 4,254,274. Equivalent compounds are listed in that patent.

The residue (XXXII) is prepared according to EP 238226 here incorporated by reference when the valence is saturated with —$CH_2COOH$. Equivalent products are reported in said patent as substituted 1,3,4,9 tetrahydropyrane [3,4-b] indole-1-acetic acids.

The residue (XXXIII) is prepared by pirazolac (the valence is saturated with —$CH_2COOH$), as indicated in EP 54,812 here incorporated by reference. Equivalent products are listed in the said patent.

The residue (XXXVI) is prepared according to the patent UK 2,035,311 here incorporated by reference, by starting from zaltoprofen having termination —$CH(CH_3)$—COO—. Equivalent products are listed in the said patent.

The process of preparation of the residue XXXVII) is obtained by starting from the Mofezolac and it is prepared according to EP 26928. Equivalent products are reported therein.

With respect to the compounds of group III), the connecting bridges $X_1$ as above defined may be obtained using the above methods of the known art or changing the known methods by introducing bridges $X_1$ when these are different from the connecting bridges described in the above patents.

The compounds wherein R is of group IV) are described in WO-95-09831 wherein the preparation methods are also described. This patent is incorporated herein in full as a reference.

In group IV) the compounds may also be obtained: for the compounds of formula (II), using patent U.S. Pat. No. 3,904,682; for the compounds of formula (X), in accordance with patent U.S. Pat. No. 4,161,538; for the compunds of formula (III), in accordance with patent U.S. Pat. No. 3,228,831. These patents are fully included in the present application as a reference.

With respect to the compounds of group IV), the connecting bridges $X_1$ as above defined may be obtained using the above methods of the known art or changing the known methods by introducing bridges $X_1$ when these are different from the connecting bridges described in the above patents.

The compounds wherein R is of group V) are described in the Italian patent MI94A 000916 wherein the methods of preparation are also described. This patent is incorporated herein in full as a reference. In group V) the compounds may also be obtained: for the compounds of formula (II), using patent U.S. Pat. No. 4,089,969 which is incorporated herein in full as a reference; for the compounds of formula (V) may be obtained in accordance with patent U.S. Pat. No. 4,556,672 which is incorporated herein in full as a reference.

The residue (X) is prepared according to German patent 2,756,113. Equivalent products are listed in the said patent.

The residue (XI) is prepared according to the patent EP 147,177 here incorporated by reference, by starting from ampiroxicam having the termination —COOC$_2$H$_5$. Equivalent products are listed in the said patent.

The residue (XII) is prepared according to J. Medicinal Chem., vol. 27, No. 11, November 1984, Walsh et al, Antiinflammatory Agents. 3. Synthesis and Pharmacological Evaluation of 2-Amino-3-Benzoylphenylacetic Acid and Analogues, here incorporated by reference. Equivalent products are listed in said publication.

The residue (XIII) is prepared by starting by the Lornoxicam, wherein the valence is saturated with H. It is prepared according to GBP 2,003,877. Equivalent products are described in said patent.

With respect to the compounds of group V), the connecting bridges $X_1$ as above defined may be obtained using the above methods of the known art or changing the known methods by introducing bridges, $X_1$ when these are different from the connecting bridges described in the above patents.

Generally, the connection between A and $X_1$ is, as we saw, generally, of the ester or amide type (NH or NR$_{1C}$, as defined in X) when R is of groups I), II), III), IV). All well known synthetic routes for forming these bonds may be used to form this connection.

In the case of esters of group I), III) and IV), the most direct synthetic route involves a reaction of acyl chlorides R—CO—Cl with halogen alcohols of the HO—Y—Cl, HO—Y—Br, HO—Y—I types, in the experimental conditions of the known art.

The reaction products of formula R—CO—O—Y—Cl (Br,I) may also be obtained for class II by reacting the sodium or potassium salts of said R—CO—OH acids with dihalogen derivatives of the general formula YCl$_2$, YBr$_2$ or YI$_2$.

The reaction products are converted into the final products by reacting with AgNO$_3$ in acetonitrile, in accordance with literature reports.

The general route for groups I), III), IV) is as follows:

R—CO—Cl+HO—Y—Br→R—CO—O—Y—Br+AgNO$_3$→A—X$_1$—NO$_2$ wherein X$_1$=YO.

The general route for group II is as follows:

R—CO—ONa+Br$_2$Y→R—CO—O—Y—Br+AgNO$_3$→A—X$_1$—NO$_2$ wherein X$_1$=YO.

In the case of amides the synthetic route involves a reaction of the same acyl chlorides RCOCl with amino alcohols of the general formula NH$_2$—Y—OH, NHR$_{1C}$—Y—OH to give amides of the general formula:

R—CO—NH—Y—OH and R—CO—NR$_{1C}$—Y—OH in accordance with known methods.

The reaction of said amides with halogenating agents such as, for example, PCl$_5$, PBr$_3$, SOCl$_2$, etc., leads to halogen derivatives of the general formula:

R—CO—NH—Y—Br(Cl) and R—CO—NR$_{1C}$—Y—Br(Cl).

These, by reacting with AgNO$_3$ in acetonitrile in accordance with known literature methods, lead to the final products A—X$_1$—NO$_2$.

The route may be outlined as follows:

PCl$_5$

R—CO—Cl+NHR$_{1C}$—Y—OH→R—CO—NR$_{1C}$—Y—OH→R—CO—NR$_{1C}$—Y—Cl+AgNO$_3$→R—CO—NR$_{1C}$—Y—ONO$_2$ wherein YO is X$_{X1}$.

An alternative route to form the esters is a reaction of the sodium or potassium salts of the acids with the nitric esters of halogen alcohols of the general formula:

NO$_2$—O—Y—Cl (Br,I)

to directly give the products of the invention.

The reaction route is as follows:

R—CO—ONa+Br—Y—ONO$_2$→R—CO—O—Y—ONO$_2$ wherein YO is X$_1$.

Synthetic routes similar to those described above can be used for products Va and Vb of group V), wherein the dihalogen derivative Br$_2$Y is reached with enolates, for example, of tenoxicam or piroxicam. The reaction products are then converted, in acetonitrile, by reacting with AgNO$_3$ in accordance with the above reaction.

The general route shown below relates to the piroxicam of formula IX in group V).

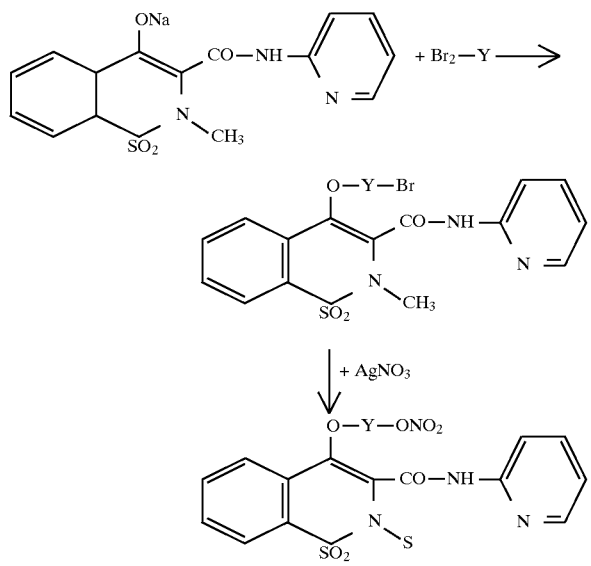

The above indicated products in the various groups are used as anti-inflammatory, analgesic, and anti-thrombotic activities. For group I) no exclusion in the meanings of $X_1$ is necessary.

For groups II), III), IV) and V), the meaning of $X_1$ is limited as above indicated for these uses, when $X_1$=—YO— for some compounds.

A further object of the invention is that it was surprisingly found that the products of the invention containing —ONO$_2$ groups are capable of having an effect inhibiting the inflammation induced by liposaccharide (LPS), and can, therefore, be used in septic shock.

This was surprising since it is well known that, generally, anti-inflammatories do not significantly change the nitrosynthetase actitivity induced by lipopolysaccharides in rats and, therefore, cannot be used in septic shock.

The products which may be used for this pharmaceutical use are the products of the general formula

A—X$_1$—NO$_2$ described above, wherein the bivalent connecting bridge $X_1$ has no limitation in this case, i.e. the known connecting bridges are not excluded as nothing was described in previous patents for this use.

It must be understood that when the compounds of the various groups contain at least one asymmetric carbon, the products can be used in racemic form or as single isomers. It is in fact well known that in the therapeutic uses of the invention in general an isomeric form is more active than the others.

The following examples are being given as an explanation not a limitation of the present invention.

EXAMPLES

Example 1

Chemical Examples—Product Preparation

Example 1a:

Preparation of compound A—$X_1$—$NO_2$, wherein R belongs to class I, $X_1$ is —$(CH_2—CH_2—O)_2$—, herein referred to as ASA.NO-DEG, and having the general formula:

2-acetoxy-benzoate of 2-[2-(nitroxy)ethoxy]ethyl

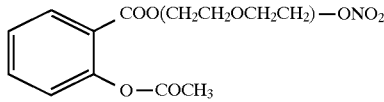

Preparation of the intermediate of the formula:
2-acetoxy-benzoate of 2-[2-(chloro)ethoxy]ethyl

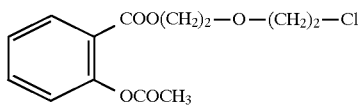

1.0 g of sodium hydride (NaH) (80% suspension in white mineral oil) was added portionwise to a solution of:
  acetylsalicylic acid 5.6 g and
  dimethylformamide 20 ml
kept at 0° C. in a stream of nitrogen.

The mixture was stirred for one hour and then added dropwise over 5 hours to a stirred solution of
  2,2'-dibromo-diethylether 10.0 g and
  dimethylformamide 15 ml
at 25° C. The mixture was stirred continuously for 3 days, then dried at reduced pressure. The residue was treated with:
  water 50 ml and
  dichloromethane 50 ml.

The phases were separated and the aqueous phase was extracted further with dichloromethane 10 ml.

The pooled organic phases were washed with water (3×25 ml), dried (MgSO$_4$), decoloured with animal charcoal (1 g), and brought to dryness in vacuum.

The residue (11.2 g) was used crude for the next reaction.
Preparation of ASA-NO-DEG:
  8.6 g of silver nitrate were added to a solution of
  ASA—$(CH_2)_2$—O—$(CH_2)_2$ Cl 11.2 g and
  acetonitrile 25 ml
kept at ambient temperature and sheltered from light.

After stirring for two days, 2.2 g of silver nitrate were added.

After another two days in the same conditions, the insoluble salts were filtered and the filtrate was freed of the solvent at reduced pressure.

A residue of 7.0 g was obtained and chromatographed on a silica gel column (500 g of silica) eluting with a toluol/ethyl acetate 95/5 v/v mixture.

The fractions which were found to be uniform by TLC (Thin Layer Chromatography) were pooled and brought to dryness. They yielded 3.0 g of ASA-NO-DEG.

A $^1$H NMR analysis (CDCl$_3$) (80 MHz) provided the following data: 2.28(3H,s); 3.7(4H,m); 4.35(2H, t); 4.52 (2H,t); 7.3 (3H,m); 7.98 (1H,dd).

The IR analysis (nujol) provided the following results. $v_{OCO}$=1780 cm$^{-1}$; $v_{COO}$=1725 cm$^{-1}$; $v_{ONO2}$=1641 e 1287 cm$^{-1}$.

Mass spectrometry gave a molecular weight value of 313.
Example 1b:

Preparation of compound A—$X_1$—$NO_2$, wherein R belongs to class II), $X_1$ is —$(CH_2—CH_2—O)_2$—, herein referred to as DICLOFENAC-NO-DEG, and having formula:

2-{N-[2,6-(dichloro)phenyl]amino}phenylacetate of 2-[2-(nitroxy)ethoxy]ethyl

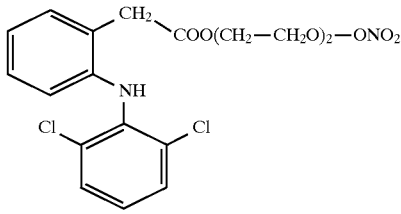

Preparation of the intermediate having formula
2-{N-[2,6-(dichloro)phenyl]amino}phenylacetate of 2-[2-(bromo)ethoxy]ethyl

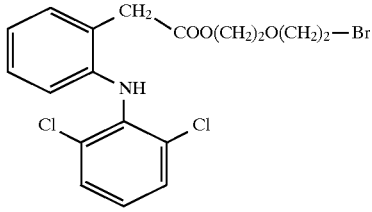

A solution of
  DICLOFENAC sodium salt 13.3 g and
  dimethylformamide 25 ml
was added to a solution of
  2,2'-dibromo-diethylether 12.3 g and
  dimethylformamide 15 ml
kept at ambient temperature in a stream of nitrogen.

The mixture was allowed to react for two days, and the solvent was then removed at reduced pressure. The residue was treated with ethyl acetate (50 ml), washed with a 5% solution of potassium carbonate (2×10 ml), then with water (20 ml), dried over anhydrous sodium sulphate. The solvent was removed at reduced pressure.

The residue weight was 16 g and was used for the next reaction with no purification.
Preparation of DICLOFENAC-NO-DEG:
  Silver nitrate 8 g in
  acetonitrile 16 ml
were added to a solution of
  DICLOFENAC —$(CH_2)_2$—O—$(CH_2)_2$—Br 16 g and
  acetonitrile 30 ml
kept at room temperature and sheltered from light.

The mixture was stirred at ambient temperature for 3 days.

Silver nitrate 3 g after 1 day
silver nitrate 3 g after 2 days
were then added.

The mixture was stirred for another 2 days. The insoluble salts were then filtered and the solvent removed from the filtrate at reduced pressure. The residue was treated with ethyl acetate (50 ml), the insoluble salts were then filtered and discarded. The solvent was removed from the filtrate at reduced pressure. A residue of 16.2 g was obtained and chromatographed on a silica gel column (700 g of silica) eluting first with toluol, then with a toluol/ethyl acetate 99/1 v/v mixture, finally with a toluol/ethyl acetate 98/2 v/v mixture.

The fractions found to be uniform by TLC analysis (thin layer chromatography) were pooled and brought to dryness to yield 4.38 g of DICLOFENAC-NO-DEG.

A $^1$H-NMR analysis (CDCl$_3$) (300 MHz) provided the following data: 3.69 (4H,t); 3.87 (2H,s); 4.3 (2H,m); 4.52 (2H,t) 6.55 (1H,d); 6.88 (1H, wide s exchanged for D$_2$O, NH); 6.97 (2H,t); 7.11 (2H,d); 7.23 (2H,d); 7.35 (2H, d).

Mass spectrometry yielded a molecular weight value of 588.

Example 1c:

Preparation of compound A—X$_1$—NO$_2$, wherein R belongs to class III) and represents the residue of the compound of formula IV, X$_1$ is —C$_6$H$_5$CH$_2$—, herein referred to as KETOPROFEN-NO-DEG, and having formula:
2-(3-benzoyl)phenylpropionate of 3-(nitroxymethyl)phenyl

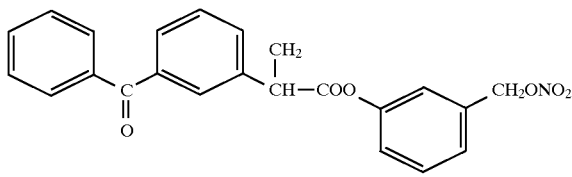

Preparation of intermediate 3-nitroxymethyl-phenol having formula:

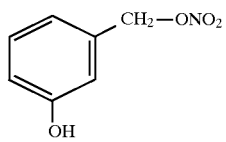

The reagents below are used in the amounts indicated and reacted as described below:
3-hydroxy-benzylalcohol 10 g
48% HBr by weight 50 ml
CH$_2$Cl$_2$ 30 ml
AgNO$_3$ 13.7 g
CH$_3$CN 70 ml 3-Hydroxy-benzylalcohol in CH$_2$Cl$_2$ was reacted with HBr at ambient temperature for 4 hours.

CH$_2$Cl$_2$ was then evaporated at reduced pressure at 30° C. after washing with an aqueous 5% NaHCO$_3$ solution and drying over anhydrous Na$_2$SO$_4$.

The oily residue was dissolved in CH$_3$CN (50 ml) and a solution of AgNO$_3$ in the remaining amount of CH$_3$CN was added dropwise. The flask was sheltered from light.

After 8 hours the AgBr precipitate was filtered and the organic phase was evaporated at reduced pressure.

The oily residue so obtained was dissolved in toluene (45 ml) and the solution was filtered on a silica gel column (400 g). The eluate was brought to dryness at reduced pressure at 30° C. to give 20 g of 3-nitroxymethylphenol.

Preparation of intermediate KETOPROFEN —COCl:
A chloride of 2-(3-benzoyl)phenyl propionic acid
KETOPROFEN 20 g
thionyl chloride 50 ml
were reacted and the solution was refluxed for 45 minutes. Thionyl chloride was evaporated off at reduced pressure. An oily yellow residue weighing 21 g was obtained and used with no further purification.

Preparation of KETOPROFEN-Ar-NO$_2$

The reagents below were used in the following amounts:
KETOPROFEN —COCl 5.45 g
3-nitroxymethylphenol 3.9 g

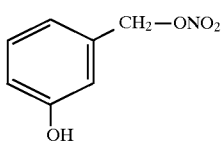

K$_2$CO$_3$ 5.5 g
AcOEt 50 ml:

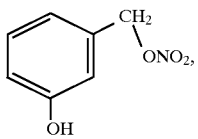

K$_2$CO$_3$ and AcOEt were added together; ketoprofen chloride was then added under nitrogen at t=0 in 30 minutes.

The whole was allowed to react for 5 hours at ambient temperature, then diluted with H$_2$O (50 ml). The organic phase was washed with 5% NaOH (2×10 ml) and evaporated off at reduced pressure. The resulting oily residue was chromatographed on silica using a toluol/EtOAc 9.5/0.5 v/v mixture as an eluant. The evaporation of the eluate gave KETOPROFEN-Ar-NO$_2$ with a yield of 85%.

A $^1$H-NMR analysis (CDCl$_3$) (300 MHz) provided the following data: 1.63 (3H,d); 4.00 (1H Q); 5.37 (2H,S); 7.01–7.89 (m,13H).

Mass spectrometry yielded a molecular weight value of 405.

Example 1d:
Preparation of compound A—X$_1$—NO$_2$, herein referred to as IBUPROFEN-NO-DEG, wherein R belongs to group IV; X$_1$ is —(CH$_2$—CH$_2$—O)$_2$—, A=RCOO, R residue of IBUPROFEN, having formula:

The same procedure of example 1a was followed, using the above R, residue of IBUPROFEN, instead of residue R of group I as shown in example 1a.

Example 1e:
Preparation of compound A—X$_1$—NO$_2$, herein referred to as FLURBIPROFEN-NO-DEG, wherein R belongs to group III; X1 is —(CH$_2$—CH$_2$—O)$_2$—, A=RCOO, R$_{3a}$=H, R$_{2a}$=CH$_3$, R having formula:

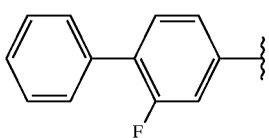

The same procedure of example 1a was followed, using the above R, residue of FLURBIPROFEN, instead of residue R of group I as shown in example 1a.

Example 1f:

Preparation of compound A—$X_1$—$NO_2$, KETOROLAC-NO-DEG, wherein R belongs to group V; $X_1$ is —($CH_2$—$CH_2$—$O$)$_2$—; A=R, R of formula II, having formula

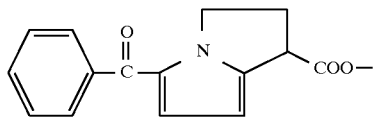

The same procedure of example 1a was followed, using the above R, residue of KETOROLAC, instead of residue R of group I as shown in example 1a.

Example 1g:

Preparation of compound A—$X_1$—$NO_2$, TIAPROFENIC ACID NO DEG, wherein R belongs to group III; $X_1$ is —($CH_2$—$CH_2$—$O$)$_2$—, A=RCOO, R is the residue of formula XXXV, wherein R is:

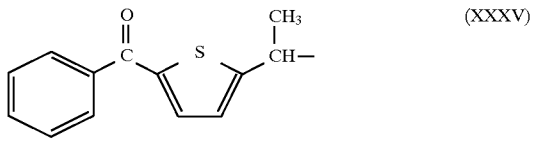

(XXXV)

The same procedure of example 1a was followed, using the above R, residue of TIAPROFENIC ACID, instead of residue R of group I as shown in example 1a.

Example 1h:

Preparation of compound A—$X_1$—$NO_2$, NAPROXEN NO-DEG, wherein R belongs to group IV; $X_1$ is —($CH_2$—$CH_2$—$O$)$_2$—, A=RCOO, R is the residue of formula II of NAPROXEN, having the general formula

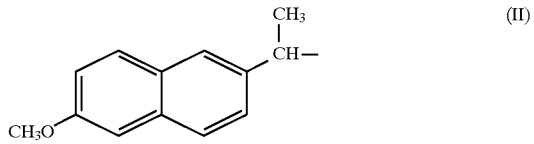

(II)

The same procedure of example 1a was followed, using the above R, residue of NAPROXEN, instead of residue R of group I as shown in example 1a.

EXAMPLE 2

Pharmacological Examples

The products used above were pharmacologically characterised.

Example 2a: ASA-NO-DEG as prepared in example 1a;

Example 2b: DICLOFENAC-NO-DEG as prepared in example 1b;

Example 2c: KETOPROFEN-NO-DEG as prepared in example 1c;

Example 2d: IBUPROFEN-NO-DEG as prepared in example 1d;

Example 2e: FLURBIPROFEN-NO-DEG as prepared in example 1e;

Example 2f: KETOROLAC NO-DEG as prepared in example 1f;

Example 2g: TIAPROFENIC ACID NO-DEG as prepared in example 1g;

Example 2h: NAPROXEN NO-DEG as prepared in example 1h.

Toxicity

Acute toxicity was evaluated by orally administering a single dose of 1, 3, 10, 30, 100 mg/Kg of produce groups of 10 mice.

The death rate and the occurence of toxic symptoms were reported over an observation period of 14 days. Even after administration of a 100 mg/Kg dose the animals showed no sign of apparent toxicity.

Anti-inflammatory activity

Anti-inflammatory activity was determined by the carrageenin-oedema method as described by Winter et al. (Proc. Soc. Exp. Biol. Med. 111, 544, 1962) in rats.

Analgesic activity

Analgesic activity was determined in Swiss mice as described by Hendershot et al. (J. Pharmacol. Exp. Therap. 125, 237, 1959).

Tolerance

Gastric tolerance was measured by oral administration to rats assessing the severity of the gastropathy induced in accordance with the criteria described by Wallace et al. (Am. J. Physiol. 259, G642, 1990).

Platelet anti-aggregating activity

Platelet anti-aggregating activity was evaluated in vitro on human platelets stimulated by thrombin in accordance with the method described by Bertele et al. (Science 220, 517, 1983).

Vasodilative activity

Vasodilative activity was determined in isolated rat aorta measuring the inhibition of the contraction induced by epinephrine in the tissue prepared in accordance with the method described by Reynolds et al. (J. Pharmacol. Exp. Therap. 252, 915, 1990).

COX Inhibition

The activity inhibiting cyclo-oxygenase was determined in isolated cells. Endothelial cells of bovine aorta were used as a source of COX-1 and macrophage line J774.2 as a source of COX-2. The same conditions described by Mitchell et al. (Proc. Nat. Acad. Sci. 90, 11693, 1993) for growth and the viability test were used.

In brief, the cells were incubated for 30 minutes with scalar concentrations of the test product and the substrate (arachidonic acid) was then added and incubated for another 15 minutes. Enzyme activity was determined radioimmunologically by measuring the formation of 6-keto-PGF 1 alpha. In the case of cell lines J.774.2, the cells were incubated for 12 hours with endotoxin to promote COX-2 formation.

Nitrosynthetase inhibition by LSP

The nitrosynthetase inhibition activity induced by lipopolysaccharide (LPS) was determined in rat neutrophils and stomach after administration of one of the test compounds and compared with that obtained after treatment of the suspension vehicle only.

In brief, Wistar rats fasting for 24 hours before treatment were orally administered the test product (10 mg/Kg) and intravenously (caudal vein) administered LPS (5 mg/Kg).

Four hours later the animals were sacrificed and the blood—for neutrophils isolation—and the stomach taken.

Enzyme activity was determined in accordance with the method described by Assreuy et al. (Br. J. Pharmacol. 108, 833, 1993).

Results:

The results obtained are described below.

As it may be observed from the data shown in tables 1 to 4, the pharmacodynamic activities (I and II in Table 1; Table 2) and the tolerance (Table 1 column III) of the nitroderivatives show a better balance as compared to natural products.

Table 4 also shows that, similarly to diclofenac nitroxybutylester, the diclofenac nitroderivative which is an object of this patent is capable of directly inhibiting cyclo-oxygenase COX-1 and COX-2, but with a significantly lower variability.

TABLE 1 (Pharmacology col.I and II; Toxicology col.III)

Study of the anti-inflammatory (I) and analgesic (II) properties (pharmacodynamics) and gastrointestinal tolerance (III) (toxicity) of the test compounds after oral administration of doses ranging from 3 to 30 mg/Kg in carboxymethylcellulose suspensions and constructing dose-response curves. The results shown are the potency ratio as compared to the reference standard.

Activities are expressed as the potency ratio compared to the natural product used as a unit standard. The nitroderivative is that of the shown examples, the natural reference compound is that shown as a reference.

TABLE 1

| TEST COMPOUND | EXAMPLE | I | II | III |
|---|---|---|---|---|
| NITRODERIVATIVE | 1a | 1.2 | 1.1 | 0.2 |
| ASPIRIN | reference | 1.0 | 1.0 | 1.0 |
| NITRODERIVATIVE | 1b | 1.3 | 0.9 | 0.3 |
| DICLOFENAC | reference | 1.0 | 1.0 | 1.0 |
| NITRODERIVATIVE | 1c | 1.0 | 1.2 | 0.1 |
| KETOPROFEN | reference | 1.0 | 1.0 | 1.0 |
| NITRODERIVATIVE | 1d | 1.0 | 1.1 | 0.1 |
| IBUPROFEN | reference | 1.0 | 1.0 | 1.0 |
| NITRODERIVATIVE | 1e | 1.0 | 1.0 | 0.1 |
| FLURBIPROFEN | reference | 1.0 | 1.0 | 1.0 |
| NITRODERIVATIVE | 1f | 1.0 | 1.0 | 0.1 |
| KETOROLAC | reference | 1.0 | 1.0 | 1.0 |
| NITRODERIVATIVE | 1g | 0.9 | 1.3 | 0.1 |
| TIAPROFENIC ACID | reference | 1.0 | 1.0 | 1.0 |
| NITRODERIVATIVE | 1h | 1.3 | 1.3 | 0.1 |
| NAPROXEN | reference | 1.0 | 1.0 | 1.0 |

TABLE 2 (Pharmacodynamic activity)

Example of the anti-cyclooxygenase (I), platelet anti-aggregating (II) and vasodilative (III) properties of the test compounds tested in vitro at concentrations in the molar range from $10^{-5}$ to $10^{-7}$ of the product in water/alcohol with the addition of small amounts of DMSO (dimethylsulphoxide). The activities are expressed as the potency ratio versus the natural product used as a unit standard, as stated in Table 1.

TABLE 2

| TEST COMPOUND | EXAMPLE | I | II | III(°) |
|---|---|---|---|---|
| NITRODERIVATIVE | 1a | 1.5 | 3.0 | 60 |
| ASPIRIN | reference | 1.0 | 1.0 | inactive |
| NITRODERIVATIVE | 1b | 1.8 | 1.8 | 50 |
| DICLOFENAC | reference | 1.0 | 1.0 | inactive |
| NITRODERIVATIVE | 1c | 1.2 | 1.8 | 50 |
| KETOPROFEN | reference | 1.0 | 1.0 | inactive |

(°) % of inhibitory action of the vasospasm induced by epinephrine

TABLE 3 (Biochemistry: Action on NOS for Septic Shock)

Study of the inhibitory properties of the nitrosynthetase (NOS) activity induced by liposaccharide (LPS) in rats using oral doses ranging from 5 to 20 mg/Kg suspended in a carboxymethylcellulose base.

TABLE 3

| TREATMENT | NOS (°°) EXAMPLE | STOMACH | NEUTROPHILS |
|---|---|---|---|
| LPS | reference | 100 | 100 |
| LPS + NITRODERIVATIVE KETOPROFEN of Ex. | 1c | 40 | 30 |
| LPS + NITROXYBUTYLKETOPROFEN | reference | 35 | 55 |
| LPS + NITRODERIVATIVE DICLOFENAC of ex. | 1b | 40 | 52 |
| LPS + NITROXYBUTYLDICLOFENAC | reference | 37 | 49 |

(°°)inhibition relative to the group treated with LPS only.

TABLE 4 (COX-Inhibition Activity)

Study of the anti-cyclooxygenase (COX-1/COX-2) properties in isolated cells.

Response expressed as a % of the controls with relative response variability.

TABLE 4

| COMPOUND | EXAMPLE | DOSE mg/ml (solution of Table 2) | COX-1 | COX-2 |
|---|---|---|---|---|
| NITRODERIVATIVE | 1b | 0.1 | 49 +/− 6 | 45 +/− 3 |
| DICLOFENAC | | 1.0 | 29 +/− 4 | 22 +/− 4 |
| DICLOFENAC | reference | 0.1 | 45 +/− 22 | 68 +/− 11 |
| NITROXYBUTYLESTER | | 1.0 | 24 +/− 10 | 41 +/− 11 |
| NITRODERIVATIVE | 1e | 0.1 | 51 +/− 5 | 47 +/− 4 |
| FLURBIPROFEN | | 1.0 | 22 +/− 3 | 18 +/− 2 |
| FLURBIPROFEN | reference | 0.1 | 48 +/− 18 | 46 +/− 23 |
| NITROXYBUTYLESTER | | 1.0 | 29 +/− 13 | 22 +/− 14 |

We claim:

1. A compound having the formula:

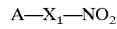

or their salts, wherein:

A=R(COX$_u$)$_t$, wherein t=0 or 1; u=0 or 1,

X=O, NH, NR$_{1C}$, wherein R$_{1C}$ is a linear or branched alkyl having 1 to 10 C atoms;

R is selected from the following groups:

group I), wherein t=1 and u=1, and R is:

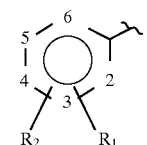

Ia)

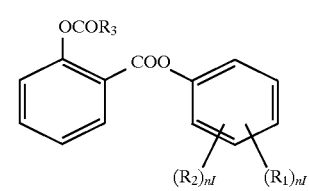

Ib)

-continued

Ic)

(structure Ic₁: aminophenol with OH and H₂N)

Ic₂) (structure: HO-phenyl(COOH)-N=N-phenyl(COOH)-OH)

Ic₃) (structure: pyridine-NHSO₂-phenyl-N=N-phenyl-OH)

wherein:

$R_1$ is an $OCOR_3$ group;

$R_3$ is methyl, ethyl or a linear or branched $C_3$–$C_5$ alkyl, or a nonaromatic or aromatic heterocycle with a single ring having 5 or 6 atoms containing one or more heteroatoms independently selected from O, N, and S;

$R_2$ is hydrogen, hydroxy, a halogen, a linear or branched alkyl having 1 to 4 C atoms, a linear or branched alkoxyl having 1 to 4 C atoms, a linear or branched perfluoroalkyl having 1 to 4 C atoms, nitro, amino, mono- or di-($C_{1-4}$) alkylamino; or $R_1$ and $R_2$ together are a dioxymethylene group, with the proviso that when X=NH, then $X_1$ is ethylene and $R_2$=H;

$R_1$ cannot be $OCOR_3$ in position 2 when $R_3$ is methyl;

nI is 0 or 1;

group II) wherein t=1 and u=1, and R is:

IIa) (diphenylamine structure with $R_{II1}$, $R_{II2}$, $R_{II3}$, $R_{II4}$, $R_{II5}$, $R_{II6}$)

IIb) (pyridine-N-phenyl structure with CH₃, CF₃)

wherein:

$R_{II5}$ is H, a linear or branched $C_1$–$C_3$ alkyl;

$R_{II6}$ is H, a linear or branched $C_1$–$C_3$ alkyl; or, when $R_{II5}$ is H, $R_{II6}$ is benzyl;

$R_{II1}$, $R_{II2}$ and $R_{II3}$, independently from one another, are H, a linear or branched $C_1$–$C_6$ alkyl or $C_1$–$C_6$ alkoxy, or Cl, F, Br;

$R_{II4}$ is $R_{II1}$ or Br;

group III), wherein t=1, u=1 and R is:

$$R_{1a}-\underset{R_{3a}}{\overset{R_{2a}}{C}}-$$

wherein:

$R_{2a}$ and $R_{3a}$ are H, a linear or branched, substituted or nonsubstituted $C_1$–$C_{12}$ alkyl, allyl, with the proviso that when one of the two groups is allyl, the other is H;

$R_{1a}$ is chosen from (II) (thiophene-C(O)-phenyl structure)

(XXI) (biphenyl-carbazole-like structure with $R_{xxi}$, $R_{xxio}$, $R_{xxi1}$)

(IV) (benzophenone structure with $R_{III1}$, $R_{III2}$)

(XXXV) (Ar-C(O)-thiophene structure)

(VI) (isoindolinone-N-phenyl structure)

(VII) ($C_6H_5O$-phenyl structure)

(VIII) (phenyl structure with $C_2H_5$, NH, $C_2H_5$, O substituents)

(IX) (2-fluorobiphenyl structure)

(X) ($H_3C$-phenyl-C(O)-N(CH₃)- structure)

-continued

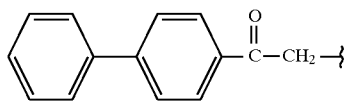
(III)

or group IIID, wherein $R_{1a}$ is:

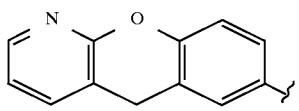
(IIIa)

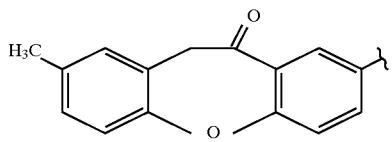
(XXX)

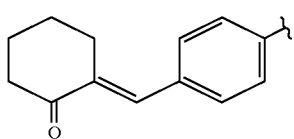
(XXXI)

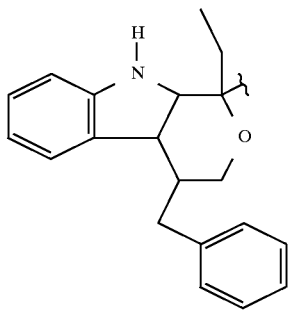
(XXXII)

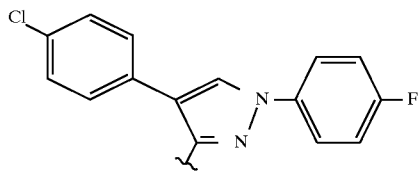
(XXXIII)

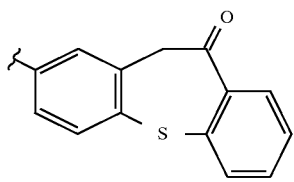
(XXXVI)

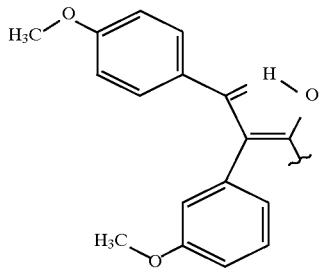
(XXXVII)

wherein in formula (IV), $R_{III1}$ is H or $SR_{III3}$, wherein $R_{III3}$ has from 1 to 4 C atoms, linear or branched;

$R_{III2}$ is H or hydroxy;

wherein in formula (XXI), $R_{XXio}$ is H, a linear or branched alkyl having from 1 to 6 C atoms, a $C_1-C_6$ alkoxycarbonyl bound to a $C_1-C_6$ alkyl, a $C_1-C_6$ carboxylalkyl, a $C_1-C_6$ alkanoyl, unsubstituted or substituted with a halogen, benzyl or halobenzyl, benzoyl or halobenzoyl;

$R_{XXi}$ is H, a halogen, hydroxy, CN, a $C_1-C_6$ alkyl, a $C_1-C_6$ alkoxy, acetyl, benzyloxy, $SR_{XXi2}$, wherein $R_{XXi2}$ is an alkyl $C_1-C_6$; a perfluoroalkyl having from 1 to 3 C atoms, a $C_1-C_6$ carboxyalkyl, $NO_2$, amino, sulphamoyl, a dialkyl sulphamoyl with the alkyl having from 1 to 6 C atoms, or a di-fluroalkyl sulphonyl with the alkyl having from 1 to 3 C atoms;

$R_{XXi1}$ is a halogen, CN, a $C_1-C_6$ alkyl, a $C_1-C_6$ alkoxy, acetyl, acetamide, benzyloxy, $SR_{III3}$ is as above defined, a perfluoroalkyl having from 1 to 3 C atoms, hydroxy, a carboxyalkyl having from 1 to 6 C atoms, $NO_2$, amino, a mono- or di-alkylamino having from 1 to 6 C atoms, sulphamoyl, a di-alkyl sulphamoyl having from 1 to 6 C atoms, or a di-fluoroalkyl sulphamoyl having from 1 to 6 atoms; or $R_{XX1}$ together with $R_{XXi1}$ is an alkylene dioxy having from 1 to 6 C atoms;

wherein in formula (XXXV), Ar is phenyl, a hydroxyphenyl unsubstituted or substituted with a halogen, an alkanoyl and an alkoxy having from 1 to 6 C atoms, a trialalkyl having from 1 to 6 C atoms, cyclo-pentyl, cylo-hexyl, cyclo-heptyl, heteroaryl, furyl, pyridyl;

group IV) wherein t=1, u=1, and R is

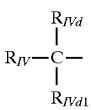

wherein:

$R_{IVd}$ and $R_{IVd1}$ are at least one H and the other a linear or branched $C_1-C_6$ alkyl, or a di-fluoroalkyl with the alkyl having from 1 to 6 C, or $R_{IVd}$ and $R_{IVd1}$ together form a methylene group;

wherein $R_{IV}$ is selected from:

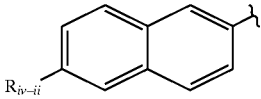
(II)

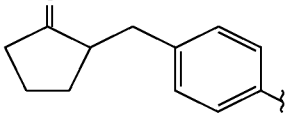
(X)

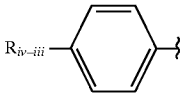
(III)

wherein in formula (II):

$R_{v-ii}$ is a 1–6 C alkyl, a cycloalkyl having from 3 to 7 C atoms, an alkoxymethyl having from 1 to 7 C atoms, a trifluroalkyl having from 1 to 3 C atoms, vinyl, ethinyl, halogen, an alkoxy having from 1 to 6 C atoms, a di-fluoroalkoxy with the alkyl having from 1 to 7 C atoms, an alkoxymethyloxy having from 1 to 7 C atoms, an alkylthiomethyloxy with the alkyl having from 1 to 7 C atoms, an alkyl methylthio with the alkyl having from 1 to 7 C atoms, cyano, di-fluoromethylthio, phenyl or phenylalkyl substituted with the alkyl having from 1 to 8 C atoms;

wherein in formula (III):

$R_{iv-iii}$ is a linear or branched $C_2-C_5$ alkyl, a $C_2$ and $C_3$ alkyloxy, allyloxy, phenoxy, phenylthio, a cycloalkyl having from 5 to 7 C atoms;

group V), R is:

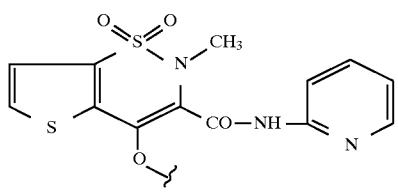 (VII)

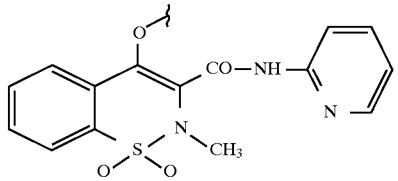 (IX)

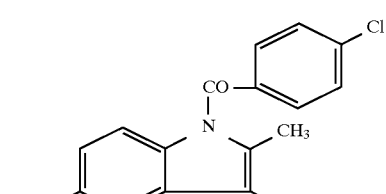 (IV)

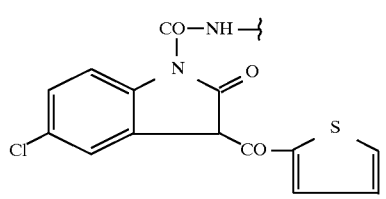 (V)

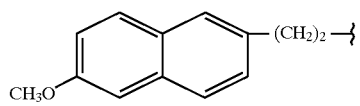 (III)

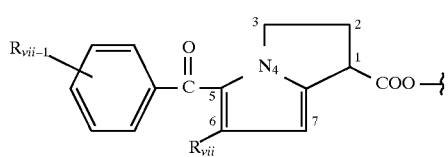 (II)

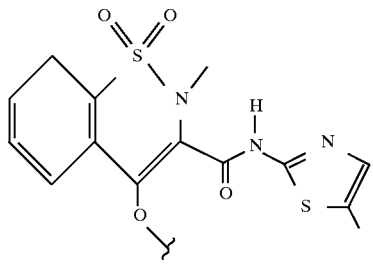 (X)

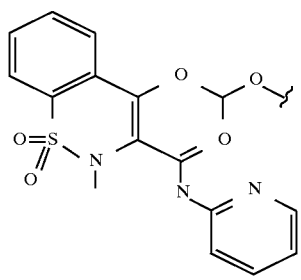 (XI)

-continued

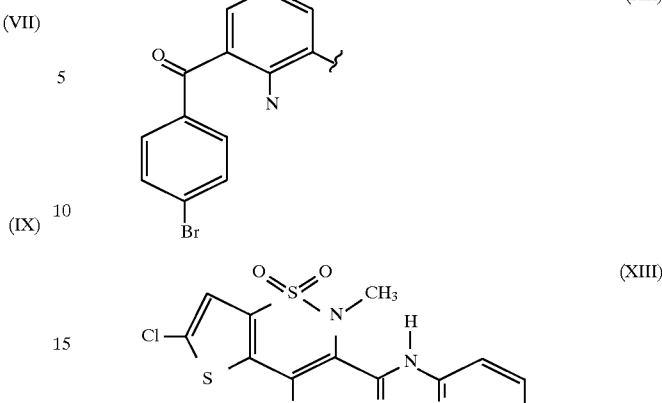

(XII)

(XIII)

wherein in the radicals of formula (II), $R_{vii}$ is H or a linear or branched alkyl having from 1 to 4 C atoms;

$R_{vii\text{-}1}$ is as defined for $R_{vii}$ or a linear or branched alkoxy having from 1 to 4 C atoms; Cl, F, Br; and the position of $R_{vii\text{-}1}$ is o-, m- or p-;

$X_1$ in the formula $A$—$X_1$—$NO_2$ is a bivalent connecting bridge selected from the following:

—YO—
wherein Y is:
  a linear or branched $C_1$–$C_{20}$ alkylene, with the proviso that the connection bridge is excluded when R is:
    a radical of group I) except radicals of formula (Ib) and (Ic);
    a radical of group II) except radicals of formula ($II_b$);
    a radical of group III) except radicals of group (IIID);
    a radical of group IV);
    a radical of group V), except radicals of formula (X) and including —$(CH_2)_4$— for the compounds of formula (III) and (IV);

or a cycloalkylene having from 5 to 7 carbon atoms, excluding this connecting bridge when R is a radical of formula (Ia) of group I;

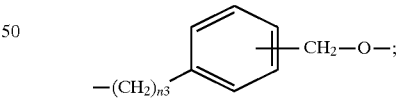

wherein $n_3$ is 0 or an integer from 1 to 3,

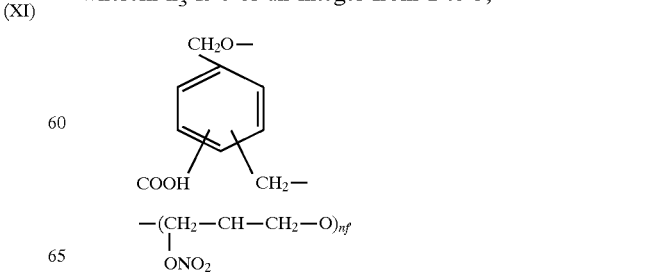

wherein nf' is an integer from 1 to 6,

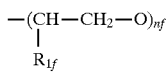

wherein $R_{1f}$=H, —$CH_3$ and nf is an integer from 1 to 6.

2. The compound according to claim 1, wherein,
in group I):
in the radicals of formula (Ia): X is O, R1 is acetoxy, $X_1$ is $(CH_2—CH_2—O)_2$, $R_2$ is hydrogen;
in the radicals of formula (Ib): $R_3$=$CH_3$, nI=O, X is equal to O, $X_1$ is ethylene;
in group II):
wherein $R_{II1}$, $R_{II2}$ and $R_{II4}$ are H, $R_{II3}$ is chlorine and $R_{II3}$ is in the ortho position relative to HN; $R_{II5}$ and $R_{II6}$ are H;
X is equal to O,
and $X_1$ is $(CH_2—CH_2—O)_2$.

3. A pharmaceutical composition containing the compound according to claim 1 or 2 in admixture with a pharmaceutically acceptable excipient.

4. A method for the treatment of septic shock which comprises administration of an effective amount of the compound having the formula:

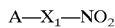

wherein A is as defined by claim 1 or 2 and $X_1$ is a bivalent connecting bridge chosen from the following:
—YO—
wherein Y is:
a linear or branched $C_1$–$C_{20}$ alkylene,
an unsubstituted or substituted cycloalkylene having from 5 to 7 carbon atoms;

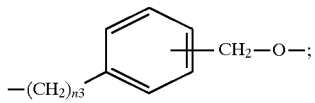

wherein $n_2$ is 0 or an integer from 1 to 3,

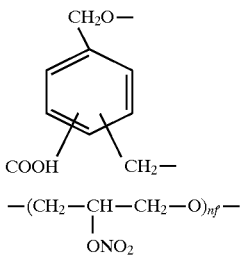

wherein nf' is an integer from 1 to 6,

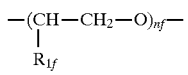

wherein $R_{1f}$=H, —$CH_3$ and nf is an integer from 1 to 6.

5. A method for the treatment of inflammation which comprises administration of an anti-inflammatory amount of a compound having general formula:

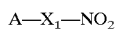

wherein A is defined by claim 1 or 2 and $X_1$ is a bivalent connecting bridge chosen from the following:

—YO—
where Y is:
a linear or branched $C_1$–$C_{20}$ alkylene, excluding this connecting bridge when R is:
a radical of group II) except radicals of formula ($II_b$);
a radical of group III) except radicals of group (IIID)
a radical of group IV);
a radical of group V), except radicals of formula (X) and including —$(CH_2)_4$— for the radicals of formulae (III) and (IV);
an unsubstituted or substituted cycloalklene having from 5 to 7 carbon atoms;

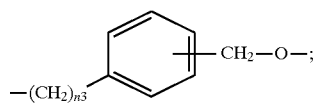

wherein $n_3$ is 0 or an integer from 1 to 3,

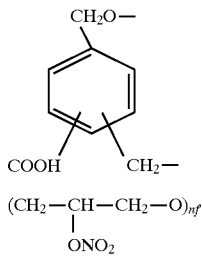

wherein nf' is an integer from 1 to 6,

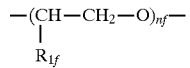

wherein $R_{1f}$=H, —$CH_3$ and nf is an integer from 1 to 6.

6. A method for anti-thrombotic treatment which comprises administration of an antithrombotic amount of a compound having the formula

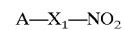

wherein A is as defined by claim 1 or 2 and $X_1$ is a bivalent connecting bridge selected from the following:
—YO—
where Y is:
a linear or branched $C_1$–$C_{20}$ alkylene, excluding this connecting bridge when R is:
a radical of group II) except radicals of formula ($II_b$);
a radical of group III) except radicals of group (IIID)
a radical of group IV);
a radical group of V), except formula (X) and including —$(CH_2)_4$— for the radicals of formulae (iii) and (IV);
a cycloalkylene having from 5 to 7 carbon atoms,

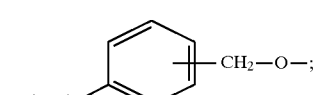

wherein $n_3$ is 0 or an integer from 1 to 3,

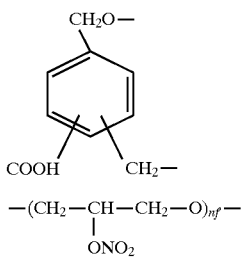

$$-(CH_2-CH-CH_2-O)_{nf'}-$$
$$\phantom{-(CH_2-CH-}|$$
$$\phantom{-(CH_2-CH}ONO_2$$

wherein nf' is an integer from 1 to 6, $$-(CH-CH_2-O)_{nf}-$$
$$\phantom{-(}|$$
$$\phantom{-(}R_{1f}$$

wherein $R_{1f}$=H, —$CH_3$ and nf is an integer from 1 to 6.

7. A method for analgesic treatment comprising administration of an analgesic amount of a compound of the general formula:

$$A-X_1-NO_2$$

wherein A is as defined by claim 1 or 2 and $X_1$ is a bivalent connecting bridge selected from the following:
—YO—
where Y is:
  a linear or branched $C_1$–$C_{20}$ alkylene, excluding this connecting bridge when R is:
    a radical of group II) except radicals of formula ($II_b$);
    a radical of group III) except radicals of group (IIID);
    a radical of group IV);
    a radical group of V), except formula (X) and including —$(CH_2)_4$— for the radicals of formulae (iii) and (IV);
  an unsubstituted or substituted cycloalkylene having from 5 to 7 carbon atoms;

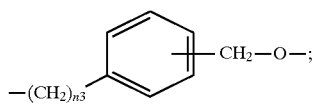

wherein $n_3$ is 0 or an integer from 1 to 3,

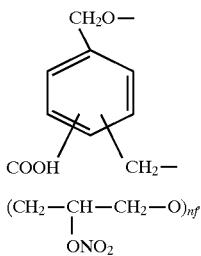

$$(CH_2-CH-CH_2-O)_{nf'}$$
$$\phantom{(CH_2-CH-}|$$
$$\phantom{(CH_2-CH}ONO_2$$

wherein nf' is an integer from 1 to 6, $$-(CH-CH_2-O)_{nf}-$$
$$\phantom{-(}|$$
$$\phantom{-(}R_{1f}$$

wherein $R_{1f}$=H, —$CH_3$ and nf is an integer from 1 to 6.

8. The compound of claim 1, wherein R is as defined by group III, formula (IV), wherein $R_{III1}$ and $R_{III2}$ are H, $R_{3a}$ is H, $R_{2a}$ is methyl, and X=O.

9. The compound of claim 1, wherein R is as defined by group III, formula (XXI), wherein $R_{XXio}$ is H, the connecting bridge is in position 2, $R_{XX1}$ is H, $R_{XX11}$ is chlorine and is in the para position relative to nitrogen; $R_{3a}$ is H, $R_{2a}$ is methyl, and X is O.

10. The compound of claim 1, wherein R is as defined by group III, formula (XXXV), wherein Ar is phenyl, $R_{3a}$ is H, $R_{2a}$ is methyl, and X is O.

11. The compound of claim 1, wherein R is as defined by group III, formula (II), wherein $R_{3a}$ is H, $R_{2a}$ is methyl, and X=O.

12. The compound of claim 1, wherein R is as defined by group III, formula (VI), wherein $R_{2a}$ is $CH_3$.

13. The compound of claim 2, wherein R is as defined by group III, formula (VI), wherein $R_{2a}$ is H, $R_{3a}$=$CH_3$, and X=O.

14. The compound of claim 1, wherein R is as defined by group III, formula (VIII), wherein $R_{2a}$=$R_{3a}$=H and X=O.

15. The compound of claim 1, wherein R is as defined by group III, formula (VII), wherein $R_{3a}$=X, $R_{2a}$=—$CH_3$ and X=O.

16. The compound of claim 1, wherein R is as defined by group III, formula (III), wherein $R_{2a}$=$R_{3a}$=H and X=O.

17. The compound of claim 1, wherein R is as defined by group III, formula (IX), wherein $R_{3a}$ is H, $R_{2a}$ is —$CH_3$ and X=O.

18. The compound of claim 1, wherein R is as defined by group III, formula (X), wherein $R_{2a}$=$R_{3a}$=H and X=O.

19. The compound of claim 1, wherein R is as defined by group III, and $R_{1a}$ is defined by group IIID, formula (IIIa), wherein $R_{2a}$=H, $R_{3a}$=—$CH_3$, u=1 and X=O.

20. The compound of claim 1, wherein R is as defined by group III, and $R_{1a}$ is defined by group IIID, formula (XXX), wherein $R_{2a}$=H, $R_{3a}$=$CH_3$, u=1 and X=O.

21. The compound of claim 1, wherein R is as defined by group III, and $R_{1a}$ is defined by group IIID, formula (XXXI) wherein $R_{2a}$=H, $R_{3a}$=$CH_3$, u=1 and X=O.

22. The compound of claim 1, wherein R is as defined by group III, and $R_{1a}$ is defined by group IIID, formula (XXXII) wherein $R_{2a}$=$R_{3a}$=H, u=1 and X=O.

23. The compound of claim 1, wherein R is as defined by group III, and $R_{1a}$ is defined by group IIID, formula (XXXIII) wherein $R_{2a}$=$R_{3a}$=H, u=1 and X=O.

24. The compound of claim 1, wherein R is as defined by group III, and $R_{1a}$ is defined by group IIID, formula (XXXVI) wherein $R_{2a}$=H, $R_{3a}$=$CH_3$, u=1 and X=O.

25. The compound of claim 1, wherein R is as defined by group III, and $R_{1a}$ is defined by group IIID, formula (XXXVII) wherein $R_{2a}$=$R_{3a}$=H, t=1 and X=O.

26. The compound of claim 1, wherein R is as defined by group IV, formula (II) wherein $R_{iv-ii}$ is $CH_3O$, $R_{ivd}$ is H and $R_{ivd1}$ is —CH3, X=NH or O and $X_1$=—$(CH_2$—$CH_2$—$O)_2$.

27. The compound of claim 1, wherein R is as defined by group IV, formula (X) wherein $R_{IVd}$ is H and $R_{IVd1}$ is —$CH_3$, X=NH or O and $X_1$ is equal to $(CH_2$—$CH_2$—$O)_2$.

28. The compound of claim 1, wherein R is as defined by group IV, formal (III), wherein $R_{IV-111}$ is

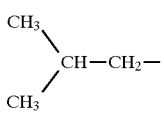

and $R_{IVd}$=H, $R_{IVd1}$ is —$CH_3$, X=NH or O and $X_1$ is equal to $(CH_2$—$CH_2$—$O)_2$.

29. The compound of claim 1, wherein R is as defined by group V, formula (II), wherein $R_{vii}$ and $R_{vii-1}$ are H, and A=R and t=0.

30. The compound of claim 1, wherein R is as defined by group V, formula (V), wherein A=R and t=0.

31. The compound of claim 1, wherein R is as defined by group V, formula (VII), wherein A is RCO and t=1 and u=0 or A is R and t=0.

32. The compound of claim 1, wherein R is as defined by group V, formula (IX), wherein A=R and t=0.

33. The compound of claim 1, wherein R is as defined by group V, formula (IX), wherein A=RCO, t=1 and u=0.

34. The compound of claim 1, wherein R is as defined by group V, formula (III) wherein A=RCOO, t=1 and u=0 or 1; or A=R and t=0.

35. The compound of claim 1, wherein R is as defined by group V, formula (III) wherein A=R and t=0.

36. The compound of claim 1, wherein R is as defined by group V, formula (IV), wherein A=RCOO, t=1, and u=1.

37. The compound of claim 1, wherein R is as defined by group V, formula (X), wherein t=0.

38. The compound of claim 1, wherein R is as defined by group V, formula (XI), wherein u=1, X=O; and t=0.

39. The compound of claim 1, wherein R is as defined by group V, formula (XII), wherein $R_{2a}=R_{3a}=H$, u=1, X=O, and t=0.

40. The compound of claim 1, wherein R is as defined by group V, formula (XIII) t=0.

* * * * *